(12) United States Patent
Chaturvedi et al.

(10) Patent No.: US 6,984,750 B2
(45) Date of Patent: Jan. 10, 2006

(54) PVD SUPPORTED MIXED METAL OXIDE CATALYST

(75) Inventors: Sanjay Chaturvedi, Lansdale, PA (US); Jingguang Chen, Hockessin, DE (US); Michael Bruce Clark, Jr., Coppersburg, PA (US); Anne Mae Gaffney, West Chester, PA (US)

(73) Assignee: Rohm and Haas Company, Philadelphia, PA (US)

( * ) Notice: Subject to any disclaimer, the term of this patent is extended or adjusted under 35 U.S.C. 154(b) by 48 days.

(21) Appl. No.: 10/460,730

(22) Filed: Jun. 12, 2003

(65) Prior Publication Data

US 2003/0236163 A1 Dec. 25, 2003

Related U.S. Application Data

(60) Provisional application No. 60/391,557, filed on Jun. 25, 2002.

(51) Int. Cl.
- C07C 253/00 (2006.01)
- B01J 21/02 (2006.01)
- B01J 21/08 (2006.01)
- B01J 23/00 (2006.01)
- B01J 20/00 (2006.01)

(52) U.S. Cl. ............. 558/323; 558/321; 558/322; 558/324; 558/325; 501/206; 501/248; 501/311; 501/312; 501/322; 501/323; 501/215; 502/255; 502/415; 502/439; 502/527.12; 502/527.15; 502/527.2; 502/527.24

(58) Field of Classification Search ........... 502/312, 502/311, 321, 322, 323, 215, 248, 255, 407, 502/415, 439, 527.12, 527.15, 527.2, 527.24, 502/206, 212; 558/322, 323, 324, 321, 325
See application file for complete search history.

(56) References Cited

U.S. PATENT DOCUMENTS

| | | | | |
|---|---|---|---|---|
| 4,051,179 A | * | 9/1977 | Sonobe et al. | 562/535 |
| 4,290,920 A | * | 9/1981 | Suresh et al. | 502/27 |
| 4,783,545 A | * | 11/1988 | Glaeser et al. | 558/319 |
| 5,231,214 A | * | 7/1993 | Ushikubo et al. | 558/319 |
| 5,281,745 A | | 1/1994 | Ushikubo et al. | |
| 5,380,933 A | | 1/1995 | Ushikubo et al. | |
| 5,422,328 A | * | 6/1995 | Ushikubo et al. | 502/312 |
| 5,472,925 A | * | 12/1995 | Ushikubo et al. | 502/312 |
| 5,559,065 A | | 9/1996 | Lauth et al. | |
| 5,750,760 A | * | 5/1998 | Ushikubo et al. | 558/319 |
| 5,907,052 A | * | 5/1999 | Hamada et al. | 558/320 |
| 6,043,185 A | | 3/2000 | Cirjak et al. | |
| 6,143,928 A | * | 11/2000 | Karim et al. | 562/534 |
| 6,239,325 B1 | * | 5/2001 | Kishimoto et al. | 585/658 |
| 6,299,668 B1 | * | 10/2001 | Penth et al. | 95/45 |
| 6,436,873 B1 | * | 8/2002 | Brocker et al. | 502/439 |
| 6,444,845 B1 | * | 9/2002 | Karim et al. | 562/535 |
| 6,461,996 B2 | * | 10/2002 | Chaturvedi et al. | 502/312 |
| 6,514,903 B2 | * | 2/2003 | Lin et al. | 502/311 |
| 6,541,664 B1 | * | 4/2003 | Jachow et al. | 562/549 |
| 6,610,629 B2 | * | 8/2003 | Hinago et al. | 502/300 |
| 6,642,174 B2 | * | 11/2003 | Gaffney et al. | 502/311 |

FOREIGN PATENT DOCUMENTS

| | | |
|---|---|---|
| EP | 0630879 B1 | 1/1998 |
| EP | 0962253 A | 12/1999 |
| EP | 1266688 A | 12/2002 |
| EP | 1172137 A | 1/2003 |
| EP | 1318127 A | 6/2003 |
| WO | WO 00/009260 | 2/2000 |
| WO | WO 00/029106 | 5/2000 |
| WO | WO 02/090308 | 11/2002 |

OTHER PUBLICATIONS

Abstract of Japanese Laid-Open Patent Application No. 6-228073 (1994)
Abstract of Japanese Laid-Open Patent Application No. 07-53448 (1995).
Abstract of Japanese Laid-Open Patent Application No. 2000-037623(Feb. 8, 2000).
A. Cybulski and J.A. Moulijn (Eds.), "Structured Catalysts and Reactors", Marcel Dekker, Inc., 1998, pp. 599-615 (Ch. 21X, Xu and J.A. Moulijn, Transformation of a Structured Carrier into Structured Catalyst).

* cited by examiner

*Primary Examiner*—Cam N. Nguyen
(74) *Attorney, Agent, or Firm*—Marcella M. Bodner; Alan Holler

(57) ABSTRACT

A supported catalyst comprising a mixed metal oxide is useful for the vapor phase oxidation of an alkane or a mixture of an alkane and an alkene to an unsaturated carboxylic acid and for the vapor phase ammoxidation of an alkane or a mixture of an alkane and an alkene to an unsaturated nitrile.

8 Claims, No Drawings

PVD SUPPORTED MIXED METAL OXIDE CATALYST

CROSS REFERENCE TO RELATED PATENT APPLICATION

This is a non-provisional application of prior pending U.S. provisional application Ser. No. 60/391,557 filed on Jun. 25, 2002.

FIELD OF THE INVENTION

The present invention relates to an improved catalyst for the oxidation of alkanes, or a mixture of alkanes and alkenes, to their corresponding unsaturated carboxylic acids by vapor phase catalytic partial oxidation; to a method of making and supporting the catalyst; and to a process for the vapor phase catalytic partial oxidation of alkanes, or a mixture of alkanes and alkenes, to their corresponding unsaturated carboxylic acids.

The present invention also relates to a method of producing unsaturated nitriles by subjecting alkanes, or a mixture of alkanes and alkenes, to vapor phase catalytic partial oxidation in the presence of ammonia.

DESCRIPTION OF RELATED ART

Nitriles, such as acrylonitrile and methacrylonitrile, have been industrially produced as important intermediates for the preparation of fibers, synthetic resins, synthetic rubbers, and the like. The most popular method for producing such nitrites is to subject an olefin such as propene or isobutene to a catalytic reaction with ammonia and oxygen in the presence of a catalyst in a gaseous phase at a high temperature. Known catalysts for conducting this reaction include a Mo—Bi—P—O catalyst, a V—Sb—O catalyst, an Sb—U—V—Ni—O catalyst, a Sb—Sn—O catalyst, a V—Sb—W—P—O catalyst and a catalyst obtained by mechanically mixing a V—Sb—W—O oxide and a Bi—Ce—Mo—W—O oxide. However, in view of the price difference between propane and propene or between isobutane and isobutene, attention has been drawn to the development of a method for producing acrylonitrile or methacrylonitrile by an ammoxidation reaction wherein a lower alkane, such as propane or isobutane, is used as a starting material, and it is catalytically reacted with ammonia and oxygen in a gaseous phase in the presence of a catalyst.

In particular, U.S. Pat. No. 5,281,745 discloses a method for producing an unsaturated nitrile comprising subjecting an alkane and ammonia in the gaseous state to catalytic oxidation in the presence of a catalyst which satisfies the conditions:

(1) the mixed metal oxide catalyst is represented by the empirical formula

wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium and, when a=1, b=0.01 to 1.0, c=0.01 to 1.0, x=0.01 to 1.0 and n is a number such that the total valency of the metal elements is satisfied; and (2) the catalyst has X-ray diffraction peaks at the following angles (±0.3°) of 2θ in its X-ray diffraction pattern: 22.1°, 28.2°, 36.2°, 45.2° and 50.0°.

Similarly, Japanese Laid-Open Patent Application Publication No. 6-228073 discloses a method of nitrile preparation comprising reacting an alkane in a gas phase contact reaction with ammonia in the presence of a mixed metal oxide catalyst of the formula

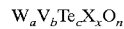

wherein X represents one or more elements selected from niobium, tantalum, titanium, aluminum, zirconium, chromium, manganese, iron, ruthenium, cobalt, rhodium, nickel, palladium, platinum, antimony, bismuth, indium and cerium and, when a=1, b=0.01 to 1.0, c=0.01 to 1.0, x=0.01 to 1.0 and n is determined by the oxide form of the elements.

U.S. Pat. No. 6,043,185 also discloses a catalyst useful in the manufacture of acrylonitrile or methacrylonitrile by the catalytic reaction in the vapor phase of a paraffin selected from propane and isobutane with molecular oxygen and ammonia by catalytic contact of the reactants in a reaction zone with a catalyst, wherein the catalyst has the empirical formula

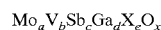

where X is one or more of As, Te, Se, Nb, Ta, W, Ti, Zr, Cr, Mn, Fe, Ru, Co, Rh, Ni, Pd, Pt, B, In, Ce, Re, Ir, Ge, Sn, Bi, Y, Pr, an alkali metal and an alkaline earth metal; and when a=1, b=0.0 to 0.99, c=0.01 to 0.9, d=0.01 to 0.5, e=0.0 to 1.0 and x is determined by the oxidation state of the cations present.

Unsaturated carboxylic acids such as acrylic acid and methacrylic acid are industrially important as starting materials for various synthetic resins, coating materials and plasticizers. Commercially, the current process for acrylic acid manufacture involves a two-step catalytic oxidation reaction starting with a propene feed. In the first stage, propene is converted to acrolein over a modified bismuth molybdate catalyst. In the second stage, acrolein product from the first stage is converted to acrylic acid using a catalyst composed of mainly molybdenum and vanadium oxides. In most cases, the catalyst formulations are proprietary to the catalyst supplier, but the technology is well established. Moreover, there is an incentive to develop a single step process to prepare the unsaturated acid from its corresponding alkene. Therefore, the prior art describes cases where complex metal oxide catalysts are utilized for the preparation of unsaturated acid from a corresponding alkene in a single step.

European Published Patent Application No. 0 630 879 B1 discloses a process for producing an unsaturated aldehyde and a carboxylic acid which comprises subjecting propene, isobutene or tertiary butanol to gas phase catalytic oxidation with molecular oxygen in the presence of (i) a catalyst composite oxide represented by the formula

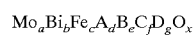

wherein A represents Ni and/or Co, B represents at least one element selected from Mn, Zn, Ca, Mg, Sn and Pb, C represents at least one element selected from P, B, As, Te, W, Sb and Si, and D represents at least one element selected from K, Rb, Cs and Tl; and wherein, when a=12, 0<b≦10, 0<c≦10, 1≦d≦10, 0≦e≦10, 0≦f≦20 and 0≦g≦2, and x has a value dependent on the oxidation state of the other elements; and (ii) a molybdenum oxide which in itself is substantially inert to said gas phase catalytic oxidation to provide the corresponding unsaturated aldehyde and unsaturated carboxylic acid. See also, European Published Patent Application No. 0 962 253 A2.

Japanese Laid-Open Patent Application Publication No. 07-053448 discloses the manufacture of acrylic acid by the gas-phase catalytic oxidation of propene in the presence of mixed metal oxides containing Mo, V, Te, O and X wherein X is at least one of Nb, Ta, W, Ti, Al, Zr, Cr, Mn, Fe, Ru, Co, Rh, Ni, Pd, Pt, Sb, Bi, B, In, Li, Na, K, Rb, Cs and Ce.

Published International Application No. WO 00/09260 discloses a catalyst for selective oxidation of propene to acrylic acid and acrolein containing a catalyst composition comprising the elements Mo, V, La, Pd, Nb and X in the following ratio:

$$Mo_aV_bLa_cPd_dNb_eX_f$$

wherein X is Cu or Cr or a mixture thereof,
a is 1,
b is 0.01 to 0.9,
c is >0 to 0.2
d is 0.0000001 to 0.2,
e is 0 to 0.2, and
f is 0 to 0.2; and wherein the numerical values of a, b, c, d, e and f represent the relative gram-atom ratios of the elements Mo, V, La, Pd, Nb and X, respectively, in the catalyst and the elements are present in combination with oxygen.

Commercial incentives also exist for producing acrylic acid using a lower cost propane feed. Therefore, the prior art describes cases wherein a mixed metal oxide catalyst is used to convert propane to acrylic acid in one step.

U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components, exclusive of oxygen, satisfy the following relationships:

$0.25 < r(Mo) < 0.98$, $0.003 < r(V) < 0.5$, $0.003 < r(Te) < 0.5$ and $0.003 < r(X) < 0.5$, wherein $r(Mo)$, $r(V)$, $r(Te)$ and $r(X)$ are the molar fractions of Mo, V, Te and X, respectively, based on the total amount of the essential components exclusive of oxygen.

Published International Application No. WO 00/29106 discloses a catalyst for selective oxidation of propane to oxygenated products including acrylic acid, acrolein and acetic acid, said catalyst system containing a catalyst composition comprising $$Mo_aV_bGa_cPd_dNb_eX_f$$

wherein X is at least one element selected from La, Te, Ge, Zn, Si, In and W,
a is 1,
b is 0.01 to 0.9,
c is >0 to 0.2,
d is 0.0000001 to 0.2,
e is >0 to 0.2, and
f is 0.0 to 0.5; and wherein the numerical values of a, b, c, d, e and f represent the relative gram-atom ratios of the elements Mo, V, Ga, Pd, Nb and X, respectively, in the catalyst and the elements are present in combination with oxygen.

Japanese Laid-Open Patent Application Publication No. 2000-037623 discloses a method for producing an unsaturated carboxylic acid comprising subjecting an alkane to a vapor phase catalytic oxidation in the presence of a catalyst having the empirical formula $$MoV_aNb_bX_cZ_dO_n$$

wherein X is at least one element selected from the group consisting of Te and Sb, Z is at least one element selected from the group consisting of W, Cr, Ta, Ti, Zr, Hf, Mn, Re, Fe, Ru, Co, Rh, Ni, Pd; Pt, Ag, Zn, B, Al, Ga, In, Ge, Sn, Pb, P, Bi, Y, rare earth elements and alkaline earth elements, $0.1 \leq a \leq 1.0$, $0.01 \leq b \leq 1.0$, $0.01 \leq c \leq 1.0$, $0 \leq d \leq 1.0$ and n is determined by the oxidation states of the other elements.

Despite the above-noted attempts to provide new and improved catalysts for the oxidation of alkanes to unsaturated carboxylic acids and for the ammoxidation of alkanes to unsaturated nitriles, one impediment to the provision of a commercially viable process for such catalytic oxidations is the identification of a catalyst providing adequate conversion and suitable selectivity, thereby providing sufficient % yield of the unsaturated product. Another limitation to the prior art is lack of providing a commercially viable, multidimensional structure onto which one may support the catalyst or into which one may formulate the catalyst.

BRIEF SUMMARY OF THE INVENTION

By the present invention, there are provided catalysts wherein the performance is enhanced by supporting the catalyst in accordance with the principles herein. In particular, the catalyst is supported by a self-supporting multidimensional support structure that is pre-formed (e.g., a foam, monolith, fabric, or otherwise) or a support (self-supporting or not) comprising $Nb_2O_5$, cordierite, partially stabilized zirconia (e.g., stabilized with MgO or CaO), ceramic fibers (e.g., oxides, such as blends of $Al_2O_3$, $SiO_2$, and boria), or mixtures thereof and then contacted with precursors of the catalyst. As used herein, "self-supporting" in the context of a support structure means that the support structure will support its own weight sufficiently so that additional structure for carrying a catalyst may be avoided at the option of the operator.

Accordingly, preferably the catalysts employed in the present invention are supported by contacting precursors of the catalyst with a pre-formed and self-supporting multidimensional support structure or contacting precursors of the catalyst with a support selected from $Nb_2O_5$, cordierite, partially stabilized zirconia, ceramic fibers, or mixtures thereof.

Thus, in a first aspect, the present invention provides a process for the preparation of a supported catalyst, the process comprising:

(a) providing a catalyst support;
(b) sequentially depositing on said support a catalyst composition comprising, in random order, as essential elements, at least one layer comprising Mo, at least one layer comprising V, at least one layer comprising Te, and at least one layer comprising X, wherein X is at least one element selected from the group consisting of Nb, Ta, W, Ti, Al, Zr, Cr, Mn, Fe, Ru, Go, Rh, Ni, Pd, Pt, Sb, Bi, B, In and Ce, to form a loaded support, said step of sequentially depositing providing relative amounts of said elements such that, after a calcination of said loaded support, the relative amounts of the elements satisfy the expression $$Mo_aV_bTe_cX_d$$

wherein a, b, c and d are the relative atomic amounts of the essential elements Mo, V, Te and X, respectively, and, when a=1, b=0.01 to 1.0, c=0.01 to 1.0 and d=0.01 to 1.0;

(c) calcining said loaded support.

In a second aspect, the present invention provides a catalyst produced by the process of the first aspect of the present invention.

In a third aspect, the present invention provides a catalytic process comprising:

(a) providing a catalyst support;

(b) sequentially depositing on said support a catalyst composition comprising, in random order, as essential elements, at least one layer comprising Mo, at least one layer comprising V, at least one layer comprising Te, and at least one layer comprising X, wherein X is at least one element selected from the group consisting of Nb, Ta, W, Ti, Al, Zr, Cr, Mn, Fe, Ru, Co, Rh, Ni, Pd, Pt, Sb, Bi, B, In and Ce, to form a loaded support, said step of sequentially depositing providing relative amounts of said elements such that, after a calcination of said loaded support, the relative amounts of the elements satisfy the expression $Mo_aV_bTe_cX_d$ 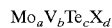

wherein a, b, c and d are the relative atomic amounts of the essential elements Mo, V, Te and X, respectively, and, when a=1, b=0.01 to 1.0, c=0.01 to 1.0 and d=0.01 to 1.0;

(c) calcining said loaded support;

(d) subjecting a feed including an alkane, or a mixture of an alkane and an alkene, to a vapor phase catalytic partial oxidation reaction in the presence of said calcined loaded support.

More specifically, the metal components of the presently contemplated catalyst may be supported on one or more suitable multi-dimensional structures, and preferably a ceramic support structure, e.g., that made of a material such as alumina, silica, silica-alumina, zirconia, titania, or the like.

DETAILED DESCRIPTION OF THE INVENTION

As discussed herein, the step of deposition is accomplished by employment of a deposition technique selected from chemical vapor deposition (CVD) or physical vapor deposition (PVD). In other words, the layers of catalyst precursor materials are applied to the support by PVD or CVD, in each case under reduced pressure, i.e. at less than 10 mbar, preferably less than 1 mbar. Possible PVD methods are vapor deposition, sputtering and anodic or cathodic arc coating. Possible CVD methods are thermal- or plasma-supported gas-phase deposition. Plasma-supported methods, such as sputtering or arc coating are preferred, sputtering being particularly preferred.

In arc coating, the coating material is removed by means of an electric arc, which leads to a high degree of ionization of the coating material in the process gas atmosphere. The support to be coated can be provided with a bias voltage, which is generally negative and leads to intensive ion bombardment during coating.

In sputtering, the materials to be coated are applied in solid form as a target to the cathode of the plasma system, sputtered under reduced pressure (preferably from $5 \times 10^{-4}$ to $1 \times 10^{-1}$ mbar) in a process gas atmosphere and deposited on the support. The process gas usually comprises a noble gas, such as argon.

Various versions of the sputtering method, such as magnetron sputtering, DC or RF sputtering, bias sputtering or reactive sputtering and combinations thereof are suitable for the production of the presently contemplated layers. In magnetron sputtering, the target to be puttered is present in an external magnetic field which concentrates the plasma in the region of the target and hence increases the sputtering rate. In DC or RF sputtering, the sputtering plasma is excited in a conventional manner by DC or RF generators. In bias sputtering, a generally negative bias voltage which leads to intensive bombardment of the support with ions during coating is applied to the support to be coated.

In reactive sputtering, reactive gases, such as hydrogen, hydrocarbons, oxygen or nitrogen are mixed in the desired amount with the process gas at a suitable time. As a result, the relevant metal oxide, nitride, carbide, carbide oxide, carbide nitride, oxide nitride or carbide oxide nitride layers can be deposited directly by sputtering a metal, for example, in the presence of hydrocarbons, oxygen and/or nitrogen, in the process gas.

The desired layer thickness, chemical composition and microstructure may be obtained, as described below, by way of controlling the deposition parameters such as process gas pressure, process gas composition, sputtering power, sputtering mode, substrate temperature and deposition time.

PVD/CVD methods allow the layer thickness to be changed in a manner which is very reproducible and, as a result of the deposition parameters (e.g., deposition rate, deposition time), simple. The layer thickness can be readily chosen from a few atomic layers to about 100 mμ. For supported catalysts, catalyst layer thicknesses are preferably from 5 nm to 50 mμ, in particular from 10 nm to 20 mμ, very particularly from 10 nm to 10 mμ, and most particularly from 10 nm to 100 nm.

PVD/CVD technologies, in particular sputtering technology, offer very considerable freedom with regard to the chemical composition of the deposited catalyst precursor layers. The spectrum of layers which can be produced ranges from two- or three- to multi-component materials. Multi-component materials are usually prepared by introducing a suitable target into the coating unit and by subsequently sputtering the target in a noble gas plasma, preferably argon. Suitable targets are homogeneous metal targets or homogeneous alloy targets, which are prepared in a known manner by melting processes or by powder metallurgy methods, or inhomogeneous mosaic targets, which are prepared by joining together smaller pieces having different chemical compositions or by placing or sticking small, disk-like material pieces on homogeneous targets. Alternatively, metallic alloys can be prepared by simultaneously sputtering two or more targets of different compositions. The supports to be coated are arranged so that they are exposed in an advantageous manner to the flow of material produced by the sputtering of the various targets. In an advantageous arrangement, the supports to be coated are passed periodically through the simultaneously burning sputtering plasmas, a layer whose composition is periodically modulated through the layer depth being applied to the supports. The modulation period may be adjusted within wide limits by the sputtering power of the individual targets and by the speed of the periodic movement of the supports. In particular, by setting a very small modulation period, it is also possible to achieve a very thorough mixing of the individual layers and hence deposition of a homogeneous alloy.

The preparation of mixed oxide, nitride or carbide systems can be carried out either by sputtering of corresponding oxide, nitride or carbide targets, or by the reactive sputtering of metal targets in corresponding reactive gas plasmas. By appropriately controlling the reactive gas flow during the reactive sputtering, it is also possible to achieve partial oxidation, nitride formation or carbide formation in the alloy layer. For example, in alloys of noble and non-noble metals, selective oxidation of the non-noble metal component can be achieved by skillful adjustment of the oxygen gas flow.

Another commonly used PVD method is the sequential PVD deposition of different metals, such as Te, Nb, V, Mo, etc. in vacuum conditions (base pressure $<1\times10^{-6}$ Torr). The metal sources are made by melting individual metal powders into different crucibles. The PVD system is typically equipped with multiple pockets that house multiple crucibles containing different metals. During PVD, an individual metal source is heated by electron beam, and the deposition rate is typically monitored using a quartz crystal balance that is located near the substrate.

With the stated deposition methods, it is also possible to produce thin gradient layers whose composition is varied in a defined manner with increasing layer depth. The variation of the composition can be controlled in a simple manner by the corresponding deposition parameters (for example, sputtering power, in the case of simultaneous sputtering, reactive gas flow, etc.). Moreover, non-periodic layer systems, e.g., layer systems comprising different metallic alloys or composite layers consisting of metallic and oxide layers, are also possible.

The microstructure (e.g., phase distribution, crystallite shape and size, crystallographic orientation) and the porosity of the layers can be controlled within wide limits by the choice of suitable deposition parameters. For example, DC magnetron sputtering of a metallic target at a pressure of from $4\times10^{-3}$ to $8\times10^{-3}$ mbar leads to very dense and hence pore-free layers, whereas a column-like morphology with increasing porosity is observed at a sputtering pressure above $1\times10^{-2}$ mbar. In addition to the sputtering pressure, the substrate temperature and any applied bias voltage have a considerable effect on the microstructure.

Examples of suitable supports are moldings of glass, quartz glass, ceramic, titanium dioxide, zirconium dioxide, alumina, aluminosilicates, borates, steatite, magnesium silicate, silica, silicates, metal, carbon (e.g., graphite), or mixtures thereof. The support may be porous or non-porous. Suitable moldings include, for example, strans, pellets, wagon wheels, stars, monolith, spheres, chips, rings or extrudates. Spheres, pellets and strands are particularly preferred.

In order to achieve uniform coating of the supports, it is advantageous to keep the supports in random motion during deposition or by the use of suitable mechanical apparatus having good flow mechanical properties. Suitable mechanical apparatus includes, e.g., periodically moved cages, drums, shells or channel in which the supports are caused to make random movements. The mechanical apparatus must, of course, have suitable openings to permit the passage of the deposition material or access by any plasma required.

In one particularly preferred aspect of the present invention, the ceramic support structure is an open or closed cell ceramic foam or monolith. More preferably, the ceramic is made from a material selected from the group consisting of cordierite, alumina, zirconia, partially stabilized zirconia (PSZ), niobium, and mixtures thereof. Of course, other like materials may also be employed. The foam structure preferably has 30 to 150 pores per inch. The monoliths may have 200 to 800 cells per inch.

These forms for the support permit high space velocities with a relatively minimal pressure drop. The skilled artisan will be familiar with such configurations and the manner of making the same, in view of teachings such as "Structured Catalysts and Reactors, A. Cybulski and J. A. Moulijn (Eds.), Marcel Dekker, Inc., 1998, p. 599–615 (Ch. 21): X. Xu and J. A. Moulijn, "Transformation of a Structured Carrier into Structured Catalyst".

Structures including a fibrous or fabric support may also be employed. For instance, ceramic oxide fabric catalyst supports, fibrous ceramic composite catalysts, or a combination, provide other attractive supported structures, which are easily formed and are readily scaled to fit commercial reactors. These types of structures, which may or may not be self-supporting, preferably will resist thermal shock under the reaction conditions of interest and will generally avoid hot-spot induced circumstances, such as a meltdown. These structures may be formed into any of a variety of three-dimensional configurations, and may employ one or more different fiber diameters, may be woven, unwoven or a mixture thereof, or even braided or otherwise aggregated into into a suitable configuration, mesh or otherwise.

It will be appreciated as to the support structures disclosed herein that plural layers may be employed, with each layer having the same or different structure, composition, orientation, or other characteristic relative to a previous layer. For instance, a catalyst bed may contain a stack or layers of fabric disks formed from ceramic oxide fabric supported catalysts or the fibrous ceramic composite catalysts. Individual layers may or may not be self-supporting. Preferably, however, the combination embodied in the overall structure is generally self-supporting. When employed herein, ceramic oxide fibers may be comprised of alumina, silica, boria, cordierite, magnesia, zirconia, or a combination of any of these oxides.

It will be appreciated that the supports of the present invention, though discussed above in the context of preferred groups of materials may be selected from any of a number of different materials, such as (without limitation) a ceramic selected from the group consisting of cordierite, alumina, zirconia, partially stabilized zirconia (PSZ), niobium, silica, boria, magnesia, titania and mixtures thereof. The groups discussed herein are thus not intended as limiting.

In another embodiment, multi-layer structures may include a stack of a plurality of perforated plates (e.g., thin, circular perforated metal disks), preferably joined together by a thermally conductive connection. The plates may be coated with an oxidation barrier, to thereby serve as thermal shock resistant catalyst supports for active catalyst materials. By way of illustration, recognizing that the teachings are applicable to other material systems or configurations, the catalyst preparation for this aspect includes fabricating a stack of thin, circular perforated metal disks and joining them together by a thermally conductive connection. The multi-disk structure is scaled at a high temperature for sufficient time to grow an alumina layer. The multi-layer structure is impregnated with the active catalyst precursor material, dried and calcined to the result in a monolith catalyst. In one example, the multi-layer structure is scaled, or pretreated, by heating in air or oxygen at 900° C. to 1200° C., for a period of time ranging from about 10–100 hours, to form a thin, tightly adhering oxide surface layer which protects the underlying support alloy from further oxidation during high temperature use. The surface layer also preferably functions as a diffusion barrier to the supported metal catalyst, thus preventing alloying of the catalyst metal with the alloy of the catalyst support. For example, the protective surface layer may be composed predominantly of alpha-alumina, but also contain a small amount of yttrium oxide. After pretreatment, the multi-layer support structure is coated with a catalyst metal, or catalyst precursor material.

The supported catalysts as described herein may be further performance tuned as desired, and may be varied in their stacking, layering, or other integration characteristics in the reactor system in such a manner to improve reaction productivity. For example, in one aspect, it may be beneficial to initially provide an oxidative dehydrogenation active catalyst (supported as described herein or unsupported) upstream in the reactor system for the conversion of an alkane to alkylene (e.g., propane to propylene) in the cases of pure, mixed and/or recycle streams. These forms might then be followed by supported or unsupported selective oxidation catalysts towards acid production.

The present mixed metal oxide catalyst (or combination of catalyst and support) can be prepared in a suitable manner such as that illustrated in the following discussion. Turning now in more specific detail to the first aspect of the present invention, the mixed metal oxide is prepared by introducing a metal and/or series of metals into a catalyst precursor admixture, such as by deposition. As discussed herein, the step of deposition is accomplished by employment of a deposition technique selected from chemical vapor deposition or physical deposition.

Generally, the metal compounds contain elements Mo, V, Te and X, as previously defined.

Once obtained, the catalyst precursor may be calcined into its desired supported form or into another suitable form. The calcination may be conducted in an oxygen-containing atmosphere or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is nitrgen or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 hr$^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired mixed metal oxide.

In a preferred mode of operation, the catalyst precursor is calcined in two stages. In the first stage, the catalyst precursor is calcined in an oxidizing environment (e.g. air) at a temperature of from 275° C. to 400° C., preferably from 275° C. to 325° C. for from 15 minute 8 hours, preferably for from 1 to 3 hours. In the second stage, the material from the first stage is calcined in a non-oxidizing environment (e.g., an inert atmosphere) at a temperature of from 500° C. to 700° C., preferably for from 550° C. to 650° C., for 15 minutes to 8 ho preferably for from 1 to 3 hours. Optionally, a reducing gas, such as, for example, ammonia or hydrogen, may be added during the second stage calcination.

In a particularly preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

With calcination, a catalyst is formed having the formula $Mo_aV_bTe_cX_dO_e$ wherein Mo is molybdenum; V is vanadium; Te is tellurium; X is as previously defined; O is oxygen; a, b, c and d are as previously defined; and e is the relative atomic amount of oxygen present in the catalyst and is dependent on the oxidation state of the other elements The oxide obtained by the above-mentioned method may be used as a final catalyst, but it may further be subjected to heat treatment usually at a temperature of from 200° to 700° C. for from 0.1 to 10 hours.

The present invention also provides, in its third aspect, a catalytic process for subjecting a feed including an alkane, or a mixture of an alkane and an alkene, to a vapor phase catalytic partial oxidation in the presence of the calcined loaded support, i.e. the so-formed catalyst. In a first embodiment, this aspect of the invention comprises a process for producing an unsaturated carboxylic acid, which comprises subjecting an alkane, or a mixture of an alkane and an alkene, to a vapor phase catalytic oxidation reaction in the presence of a supported catalyst containing the above mixed metal oxide, to produce an unsaturated carboxylic acid.

In the production of such an unsaturated carboxylic acid, it is preferred to employ a starting material gas that contains steam. In such a case, as a starting material gas to be supplied to the reaction system, a gas mixture comprising a steam-containing alkane, or a steam-containing mixture of alkane and alkene, and an oxygen-containing gas, is usually used. However, the steam-containing alkane, or the steam-containing mixture of alkane and alkene, and the oxygen-containing gas may be alternately supplied to the reaction system. The steam to be employed may be present in the form of steam gas in the reaction system, and the manner of its introduction is not particularly limited.

Further, as a diluting gas, an inert gas such as nitrogen, nitrgen or helium may be supplied. The molar ratio (alkane or mixture of alkane and alkene):(oxygen):(diluting gas):(H$_2$O) in the starting material gas is preferably (1):(0.1 to 10):(0 to 20):(0.2 to 70), more preferably (1):(1 to 5.0):(0 to 10):(5 to 40).

When steam is supplied together with the alkane, or the mixture of alkane and alkene, as starting material gas, the selectivity for an unsaturated carboxylic acid is distinctly improved, and the unsaturated carboxylic acid can be obtained from the alkane, or mixture of alkane and alkene, in good yield simply by contacting in one stage. However, the conventional technique utilizes a diluting gas such as nitrogen, nitrgen or helium for the purpose of diluting the starting material. As such a diluting gas, to adjust the space velocity, the oxygen partial pressure and the steam partial pressure, an inert gas such as nitrogen, argon or helium may be used together with the steam.

As the starting material alkane it is preferred to employ a C$_{3-8}$ alkane, particularly propane, isobutane or n-butane; more preferably, propane or isobutane; most preferably, propane. According to the present invention, from such an alkane, an unsaturated carboxylic acid such as an α,β-unsaturated carboxylic acid can be obtained in good yield. For example, when propane or isobutane is used as the starting material alkane, acrylic acid or methacrylic acid will be obtained, respectively, in good yield.

In the present invention, as the starting material mixture of alkane and alkene, it is preferred to employ a mixture of C$_{3-8}$ alkane and C$_{3-8}$ alkene, particularly propane and propene, isobutane and isobutene or n-butane and n-butene. As the starting material mixture of alkane and alkene, propane and propene or isobutane and isobutene are more preferred. Most preferred is a mixture of propane and propene. According to the present invention, from such a mixture of an alkane and an alkene, an unsaturated carboxylic acid such as an (α,β-unsaturated carboxylic acid can be obtained in good yield. For example, when propane and propene or isobutane and isobutene are used as the starting material mixture of alkane and alkene, acrylic acid or methacrylic acid will be obtained, respectively, in good yield. Preferably, in the mixture of alkane and alkene, the alkene is present in an amount of at least 0.5% by weight, more preferably at least 1.0% by weight to 95% by weight; most preferably, 3% by weight to 90% by weight.

As an alternative, an alkanol, such as isobutanol, which will dehydrate under the reaction conditions to form its corresponding alkene, i.e. isobutene, may also be used as a feed to the present process or in conjunction with the previously mentioned feed streams.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of the present invention is not clearly understood, but the oxidation reaction is carried out by oxygen atoms present in the above mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only an alkane, or a mixture of alkane and alkene, substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide with the catalyst in the regenerator usually at a temperature of from 300° to 600° C.

A process for producing an unsaturated carboxylic acid may also be employed where propane is used as the starting material alkane, and air is used as the oxygen source. In such an instance, the reaction system may be preferably a fixed bed system. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, or to mixtures of alkanes and alkenes such as propane and propene, the composition of the feed gas may be selected in accordance with the conditions for propane.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 1000° C., but is usually in the range of from 200° C. to 850° C., more preferably 250° C. to 750° C., most preferably 300° C. to 700° C.; the gas space velocity, SV, in the vapor phase reaction is usually within a range of from 100 to 1,000,000 hr$^{-1}$, preferably 300 to 600,000 hr$^{-1}$, more preferably 300 to 300,000 hr$^{-1}$; the average contact time with the catalyst can be from 0.001 to 10 seconds or more, but is usually in the range of from 0.005 to 10 seconds, preferably from 0.01 to 6 seconds; the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem, which enables the attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, nitrgen or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the promoted mixed metal oxide-containing catalyst of the present invention or by subjecting it to a vapor phase catalytic oxidation reaction with a conventional oxidation reaction catalyst for an unsaturated aldehyde.

In a second embodiment of the third aspect of the invention the process comprises subjecting an alkane, or a mixture of an alkane and an alkene, to a vapor phase catalytic oxidation reaction with ammonia in the presence of a supported catalyst containing the above mixed metal oxide, to produce an unsaturated nitrile.

In the production of such an unsaturated nitrile, as the starting material alkane, it is preferred to employ a $C_{3-8}$alkane such as propane, butane, isobutane, pentane, hexane and heptane. However, in view of the industrial application of nitriles to be produced, it is preferred to employ a lower alkane having 3 or 4 carbon atoms, particularly propane and isobutane.

Similarly, as the starting material mixture of alkane and alkene, it is preferred to employ a mixture of $C_{3-8}$alkane and $C_{3-8}$alkene such as propane and propene, butane and butene, isobutane and isobutene, pentane and pentene, hexane and hexene, and heptane and heptene. However, in view of the industrial application of nitriles to be produced, it is more preferred to employ a mixture of a lower alkane having 3 or 4 carbon atoms and a lower alkene having 3 or 4 carbon atoms, particularly propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the ammoxidation reaction of this aspect of the present invention is not clearly understood. However, the oxidation reaction is conducted by the oxygen atoms present in the above mixed metal oxide or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising an alkane, or a mixture of an alkane and an alkene, ammonia and an oxygen-containing gas, However, a gas mixture comprising an alkane or a mixture of an alkane and an alkene and ammonia, and an oxygen-containing gas may be supplied alternately.

When the gas phase catalytic reaction is conducted using an alkane, or a mixture of an alkane and an alkene, and ammonia substantially free from molecular oxygen, as the feed gas, it is advisable to employ a method wherein a part of the catalyst is periodically withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

A process may also be employed where propane is used as the starting material alkane, and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the conditions for propane.

The process of the third aspect of the present invention may be conducted at a temperature of, for example, from 250° C. to 850° C. More preferably, the temperature is from 300° C. to 800° C. The gas space velocity, SV, in the gas phase reaction is usually within the range of from 100 to 1,000,000 $hr^{-1}$, preferably from 300 to 600,000 $hr^{-1}$, more preferably from 300 to 200,000 $hr^{-1}$. As a diluent gas, for adjusting the space velocity and the oxygen partial pressure, an inert gas such as nitrogen, nitrgen or helium can be employed. When ammoxidation of propane is conducted by the method of the present invention, in addition to acrylonitrile, carbon monoxide, carbon dioxide, acetonitrile, hydrocyanic acid and acrolein may form as by-products.

The examples set forth below are for illustrative purposes only and should not be considered as limiting the scope of the invention. For purposes of this application, "% conversion" is equal to (moles of consumed alkane (or alkane/alkene)/moles of supplied alkane (or alkane/alkene))×100; and "% yield" is equal to (moles of formed desired unsaturated carboxylic acid or aldehyde/moles of supplied alkane (or alkane/alkene))×(carbon number of formed desired unsaturated carboxylic acid or aldehyde/carbon number of the supplied alkane (or alkane/alkene))×100. In addition, for each of the following examples, a honey comb substrate made of cordierite was used as the multi-dimensional catalyst support.

EXAMPLE 1

The catalyst samples were prepared as follows. The sequential physical vapor deposition (PVD) of Te, Nb, V, and Mo on a honeycomb substrate was performed in a PVD system with a base pressure of $5 \times 10^{-7}$ Torr. The metal sources were made by melting individual metal powders into different crucibles. The PVD system was equipped with four pockets that house four crucibles containing Te, Nb, V and Mo, respectively. (The unique advantage of having four metal sources at the same time is that the sequential deposition can be performed without opening the vacuum system to change metal sources.) During deposition an individual metal source was heated by electron beam, and the deposition rate (typically a few nanometers per minute) was monitored using a quartz crystal balance that was located near the honeycomb substrate. Two PVD samples were sequentially deposited using the following two sequences:

Sample 1—Mo(72 nm)/V(19 nm)/Nb(10 nm)/Te(36 nm)
Sample 2—Te(36 nm)/Nb(10 nm)/V(19 nm)/Mo(72 nm)

The two PVD samples were each calcined in a quartz tube. Each quartz tube was placed in an oven, at ambient temperature, with a 100 cc/min flow of air through the tube, the furnace was then heated from ambient temperature to 275° C. at 10° C./min and held there for one hour; then, using a 100 cc/min flow of nitrogen through the tube, the oven was heated from 275° C. to 600° C. at 2° C./min and held there for two hours.

The calcined PVD samples were each evaluated in a fixed bed reactor at a contact time of 50 milliseconds and with a feed of 7% propane, 22% steam and the balance air with results given in Table 1. Results were consistently reproduced with mass balances within 98–102%.

TABLE 1

| Catalyst Sequence | Temp. ° C. | % C3 Conv. | % AA Yield | % C3 = Yield |
|---|---|---|---|---|
| Sample 1 | 560 | 26 | 19 | 4 |
| Sample 2 | 480 | 32 | 21 | 3 |

EXAMPLE 2

The sequential PVD of Mo, V, Te and Ti on a honeycomb support is performed in a PVD system with a base pressure of $5 \times 10^{-7}$ Torr. The metal sources are made by melting individual metal powders into different crucibles. The PVD system is equipped with four pockets that house four crucibles containing Mo, V, Te and Ti, respectively. During deposition the individual metal source is heated by electron beam, and the deposition rate (typically a few nanometers per minute) is monitored using a quartz crystal balance that is located near the honeycomb substrate. The PVD sample is sequentially deposited using the following sequence:

Mo(72 nm)/V(19 nm)/Te(36 nm)/Ti(10 nm)

The PVD sample is calcined in a quartz tube. The quartz tube is placed in an oven, at ambient temperature, with a 100 cc/min flow of air through the tube, the furnace is heated from ambient temperature to 275° C. at 10° C./min and is held there for one hour; using a 100 cc/min flow of nitrogen through the tube, the oven is heated from 275° C. to 600° C. at 2° C./min and is held there for two hours.

The calcined PVD sample is evaluated in a fixed bed reactor at a contact time of 50 milliseconds and with a feed of 7% propane, 22% steam and the balance air. Consistent results are reproducible with mass balances within 98–102% and are essentially equivalent to those of Example 1/Sample 1.

EXAMPLE 3

The sequential PVD of Mo, V, Te and Ta on a honeycomb support is performed in a PVD system with a base pressure of $5 \times 10^{-7}$ Torr. The metal sources are made by melting individual metal powders into different crucibles. The PVD system is equipped with four pockets that house four crucibles containing Mo, V, Te and Ta, respectively. During deposition the individual metal source is heated by electron beam, and the deposition rate (typically a few nanometers per minute) is monitored using a quartz crystal balance that is located near the honeycomb substrate. The PVD sample is sequentially deposited using the following sequence:

Mo(72 nm)/V(19 nm)/Te(36 nm)/Ta(10 nm)

The PVD sample is calcined in a quartz tube. The quartz tube is placed in an oven, at ambient temperature, with a 100 cc/min flow of air through the tube, the furnace is heated from ambient temperature to 275° C. at 10° C./min and is held there for one hour; using a 100 cc/min flow of nitrgen through the tube, the oven is heated from 275° C. to 600° C. at 2° C./min and is held there for two hours.

The calcined PVD sample is evaluated in a fixed bed reactor at a contact time of 50 milliseconds and with a feed of 7% propane, 22% steam and the balance air. Consistent results are reproducible with mass balances within 98–102% and are essentially equivalent to those of Example 1/Sample 1.

EXAMPLE 4

The sequential PVD of Mo, V, Te and W on a honeycomb support is performed in a PVD system with a base pressure of $5 \times 10^{-7}$ Torr. The metal sources are made by melting individual metal powders into different crucibles. The PVD system is equipped with four pockets that house four crucibles containing Mo, V, Te and W, respectively. During deposition the individual metal source is heated by electron beam, and the deposition rate (typically a few nanometers per minute) is monitored using a quartz crystal balance that is located near the honeycomb substrate. The PVD sample is sequentially deposited using the following sequence:

Mo(72 nm)/V(19 nm)/Te(36 nm)/W(10 nm)

The PVD sample is calcined in a quartz tube. The quartz tube is placed in an oven, at ambient temperature, with a 100 cc/min flow of air through the tube, the furnace is heated from ambient temperature to 275° C. at 10° C./min and is held there for one hour; using a 100 cc/min flow of nitrogen through the tube, the oven is heated from 275° C. to 600° C. at 2° C./min and is held there for two hours.

The calcined PVD sample is evaluated in a fixed bed reactor at a contact time of 50 milliseconds and with a feed of 7% propane, 22% steam and the balance air. Consistent results are reproducible with mass balances within 98–102% and are essentially equivalent to those of Example 1/Sample 1.

EXAMPLE 5

The sequential PVD of Mo, V, Te and Mn on a honeycomb support is performed in a PVD system with a base pressure of $5 \times 10^{-7}$ Torr. The metal sources are made by melting individual metal powders into different crucibles. The PVD system is equipped with four pockets that house four crucibles containing Mo, V, Te and Mn, respectively. During deposition the individual metal source is heated by electron beam, and the deposition rate (typically a few nanometers per minute) is monitored using a quartz crystal balance that is located near the honeycomb substrate. The PVD sample is sequentially deposited using the following sequence:

Mo(72 nm)/V(19 nm)/Te(36 nm)/Mn(10 nm)

The PVD sample is calcined in a quartz tube. The quartz tube is placed in an oven, at ambient temperature, with a 100 cc/min flow of air through the tube, the furnace is heated from ambient temperature to 275° C. at 10° C./min and is held there for one hour; using a 100 cc/min flow of nitrogen through the tube, the oven is heated from 275° C. to 600° C. at 2° C./min and is held there for two hours.

The calcined PVD sample is evaluated in a fixed bed reactor at a contact time of 50 milliseconds and with a feed of 7% propane, 22% steam and the balance air. Consistent results are reproducible with mass balances within 98–102% and are essentially equivalent to those of Example 1/Sample 1.

EXAMPLE 6

The sequential PVD of Mo, V, Te and Ru on a honeycomb support is performed in a PVD system with a base pressure of $5 \times 10^{-7}$ Torr. The metal sources are made by melting individual metal powders into different crucibles. The PVD system is equipped with four pockets that house four crucibles containing Mo, V, Te and Ru, respectively. During deposition the individual metal source is heated by electron beam, and the deposition rate (typically a few, nanometers per minute) is monitored using a quartz crystal balance that is located near the honeycomb substrate. The PVD sample is sequentially deposited using the following sequence:

Mo(72 nm)/V(19 nm)/Te(36 nm)/Ru(10 nm)

The PVD sample is calcined in a quartz tube. The quartz tube is placed in an oven, at ambient temperature, with a 100 cc/min flow of air through the tube, the furnace is heated from ambient temperature to 275° C. at 10° C./min and is held there for one hour; using a 100 cc/min flow of nitorgen through the tube, the oven is heated from 275° C. to 600° C. at 2° C./min and is held there for two hours.

The calcined PVD sample is evaluated in a fixed bed reactor at a contact time of 50 milliseconds and with a feed of 7% propane, 22% steam and the balance air. Consistent results are reproducible with mass balances within 98–102% and are essentially equivalent to those of Example 1/Sample 1.

EXAMPLE 7

The sequential PVD of Mo, V, Te and Co on a honeycomb support is performed in a PVD system with a base pressure of $5 \times 10^{-7}$ Torr. The metal sources are made by melting individual metal powders into different crucibles. The PVD system is equipped with four pockets that house four crucibles containing Mo, V, Te and Co, respectively. During deposition the individual metal source is heated by electron beam, and the deposition rate (typically a few nanometers per minute) is monitored using a quartz crystl balance that is located near the honeycomb substrate. The PVD sample is sequentially deposited using the following sequence:

Mo(72 nm)/V(19 nm)/Te(36 nm)/Co(10 nm)

The PVD sample is calcined in a quartz tube. The quartz tube is placed in an oven, at ambient temperature, with a 100 cc/min flow of air through the tube, the furnace is heated from ambient temperature to 275° C. at 10° C./min and is held there for one hour; using a 100 cc/min flow of nitrogen through the tube, the oven is heated from 275° C. to 600° C. at 2° C./min and is held there for two hours.

The calcined PVD sample is evaluated in a fixed bed reactor at a contact time of 50 milliseconds and with a feed of 7% propane, 22% steam and the balance air. Consistent results are reproducible with mass balances within 98–102% and are essentially equivalent to those of Example 1/Sample 1.

EXAMPLE 8

The sequential PVD of Mo, V, Te and Pd on a honeycomb support is performed in a PVD system with a base pressure of $5 \times 10^{-7}$ Torr. The metal sources are made by melting individual metal powders into different crucibles. The PVD system is equipped with four pockets that house four crucibles containing Mo, V, Te and Pd, respectively. During deposition the individual metal source is heated by electron beam, and the deposition rate (typically a few nanometers per minute) is monitored using a quartz crystal balance that is located near the honeycomb substrate. The PVD sample is sequentially deposited using the following sequence:

Mo(72 nm)/V(19 nm)/Te(36 nm)/Pd(10 nm)

The PVD sample is calcined in a quartz tube. The quartz tube is placed in an oven, at ambient temperature, with a 100 cc/min flow of air through the tube, the furnace is heated from ambient temperature to 275° C. at 10° C./min and is held there for one hour; using a 100 cc/min flow of nitrogen through the tube, the oven is heated from 275° C. to 600° C. at 2° C./min and is held there for two hours.

The calcined PVD sample is evaluated in a fixed bed reactor at a contact time of 50 milliseconds and with a feed of 7% propane, 22% steam and the balance air. Consistent results are reproducible with mass balances within 98–102% and are essentially equivalent to those of Example 1/Sample 1.

EXAMPLE 9

The sequential PVD of Mo, V, Te and In on a honeycomb support is performed in a PVD system with a base pressure of $5 \times 10^{-7}$ Torr. The metal sources are made by melting individual metal powders into different crucibles. The PVD system is equipped with four pockets that house four crucibles containing Mo, V, Te and In, respectively. During deposition the individual metal source is heated by electron beam, and the deposition rate (typically a few nanometers per minute) is monitored using a quartz crystl balance that is located near the honeycomb substrate. The PVD sample is sequentially deposited using the following sequence:

Mo(72 nm)/V(19 nm)/Te(36 nm)/In(10 nm)

The PVD sample is calcined in a quartz tube. The quartz tube is placed in an oven, at ambient temperature, with a 100 cc/min flow of air through the tube, the furnace is heated from ambient temperature to 275° C. at 10° C./min and is held there for one hour; using a 100 cc/min flow of nitrogen through the tube, the oven is heated from 275° C. to 600° C. at 2° C./min and is held there for two hours.

The calcined PVD sample is evaluated in a fixed bed reactor at a contact time of 50 milliseconds and with a feed of 7% propane, 22% steam and the balance air. Consistent results are reproducible with mass balances within 98–102% and are essentially equivalent to those of Example 1/Sample 1.

EXAMPLE 10

The sequential PVD of Mo, V, Te and Sb on a honeycomb support is performed in a PVD system with a base pressure of 5×10⁻⁷ Torr. The metal sources are made by melting individual metal powders into different crucibles. The PVD system is equipped with four pockets that house four crucibles containing Mo, V, Te and Sb, respectively. During deposition the individual metal source is heated by electron beam, and the deposition rate (typically a few nanometers per minute) is monitored using a quartz crystl balance that is located near the honeycomb substrate. The PVD sample is sequentially deposited using the following sequence:

Mo(72 nm)/V(19 nm)/Te(36 nm)/Sb(10 nm)

The PVD sample is calcined in a quartz tube. The quartz tube is placed in an oven, at ambient temperature, with a 100 cc/min flow of air through the tube, the furnace is heated from ambient temperature to 275° C. at 10° C./min and is held there for one hour; using a 100 cc/min flow of nitrogen through the tube, the oven is heated from 275° C. to 600° C. at 2° C./min and is held there for two hours.

The calcined PVD sample is evaluated in a fixed bed reactor at a contact time of 50 milliseconds and with a feed of 7% propane, 22% steam and the balance air. Consistent results are reproducible with mass balances within 98–102% and are essentially equivalent to those of Example 1/Sample 1.

EXAMPLE 11

The sequential PVD of Mo, V, Te and Al on a honeycomb support is performed in a PVD system with a base pressure of 5×10⁻⁷ Torr. The metal sources are made by melting individual metal powders into different crucibles. The PVD system is equipped with four pockets that house four crucibles containing Mo, V, Te and Al, respectively. During deposition the individual metal source is heated by electron beam, and the deposition rate (typically a few nanometers per minute) is monitored using a quartz crystl balance that is located near the honeycomb substrate. The PVD sample is sequentially deposited using the following sequence:

Mo(72 nm)/V(19 nm)/Te(36 nm)/Al(10 nm)

The PVD sample is calcined in a quartz tube. The quartz tube is placed in an oven, at ambient temperature, with a 100 cc/min flow of air through the tube, the furnace is heated from ambient temperature to 275° C. at 10° C./min and is held there for one hour; using a 100 cc/min flow of nitrogen through the tube, the oven is heated from 275° C. to 600° C. at 2° C./min and is held there for two hours.

The calcined PVD sample is evaluated in a fixed bed reactor at a contact time of 50 milliseconds and with a feed of 7% propane, 22% steam and the balance air. Consistent results are reproducible with mass balances within 98–102% and are essentially equivalent to those of Example 1/Sample 1.

While the invention has been described in conjunction with the specific embodiments set forth above, it is evident that many alternatives, modifications and variations will be apparent to those skilled in the art in light of the foregoing description. Accordingly, it is intended to embrace all such alterations, modifications and variations as fall within the spirit and broad scope of the appended claims.

What is claimed is:

1. A process for the preparation of a supported catalyst, the process comprising:
  (a) providing a catalyst support;
  (b) sequentially depositing on said support a catalyst composition comprising, in random order, as essential elements, at least one layer comprising Mo, at least one layer comprising V, at least one layer comprising Te, and at least one layer comprising X, wherein X is at least one element selected from the group consisting of Nb, Ta, W, Ti, Al, Zr, Cr, Mn, Fe, Ru, Co, Rh, Ni, Pd, Pt, Sb, Bi, B, In and Ce, to form a loaded support, said step of sequentially depositing providing relative amounts of said elements such that, after a calcination of said loaded support, the relative amounts of the elements satisfy the expression $Mo_aV_bTe_cX_d$ wherein a, b, c and d are the relative atomic amounts of the essential elements Mo, V, Te and X, respectively, and, when a=1, b=0.01 to 1.0, c=0.01 to 1.0 and d=0.01 to 1.0;
  (c) calcining said loaded support.

2. The process according to claim 1, wherein said catalyst support is a self supporting multidimensional support structure.

3. The process according to claim 2, wherein said self-supporting multidimensional support structure comprises a foam, a monolith, a fabric or mixture thereof.

4. The process according to claim 2, wherein said self-supporting multidimensional support structure comprises a ceramic material selected from the group consisting of cordierite, alumina, zirconia, partially stabilized zirconia (PSZ), niobium oxide, silica, boria, magnesia, titania and mixtures thereof.

5. The process according to claim 2, wherein said self-supporting multidimensional support structure comprises a woven fabric.

6. The process of claim 2, wherein said self-supporting multidimensional support structure comprises a plurality of layers joined by a thermal conductor.

7. A catalytic process comprising:
  (a) providing a catalyst support;
  (b) sequentially depositing on said support a catalyst composition comprising, in random order, as essential elements, at least one layer comprising Mo, at least one layer comprising V, at least one layer comprising Te, and at least one layer comprising X, wherein X is at least one element selected from the group consisting of Nb, Ta, W, Ti, Al, Zr, Cr, Mn, Fe, Ru, Co, Rh, Ni, Pd, Pt, Sb, Bi, B, In and Ce, to form a loaded support, said step of sequentially depositing providing relative amounts of said elements such that, after a calcination of said loaded support, the relative amounts of the elements satisfy the expression $Mo_aV_bTe_cX_d$ wherein a, b, c and d are the relative atomic amounts of the essential elements Mo, V, Te and X, respectively, and, when a=1, b=0.01 to 1.0, c=0.01 to 1.0 and d=0.01 to 1.0;
  (c) calcining said loaded support;
  (d) subjecting a feed including an alkane or a mixture of an alkane and an alkene to a vapor phase catalytic partial oxidation reaction in the presence of said calcined loaded support.

8. The process according to claim 7, wherein said feed further includes ammonia.

* * * * *